United States Patent
Cull

(10) Patent No.: US 8,579,851 B2
(45) Date of Patent: Nov. 12, 2013

(54) SURGICAL SYSTEM HAVING MEANS FOR ISOLATING VACUUM PUMP

(75) Inventor: Laurence J. Cull, Wildwood, MO (US)

(73) Assignee: Bausch & Lomb Incorporated, Rochester, NY (US)

( * ) Notice: Subject to any disclaimer, the term of this patent is extended or adjusted under 35 U.S.C. 154(b) by 1459 days.

(21) Appl. No.: 11/961,302

(22) Filed: Dec. 20, 2007

(65) Prior Publication Data

US 2009/0163852 A1  Jun. 25, 2009

(51) Int. Cl.
 *A61M 1/00* (2006.01)
(52) U.S. Cl.
 USPC .................................. 604/35; 604/30; 604/67
(58) Field of Classification Search
 USPC ......... 604/27, 28, 30–35, 43–45, 65, 67, 118, 604/119, 151, 294, 297, 319, 320, 521, 604/902; 417/477.2
 See application file for complete search history.

(56) References Cited

U.S. PATENT DOCUMENTS

| | | | |
|---|---|---|---|
| 3,693,613 A * | 9/1972 | Kelman | 606/169 |
| 3,902,495 A | 9/1975 | Weiss et al. | 128/276 |
| 4,592,741 A * | 6/1986 | Vincent | 604/35 |
| 4,832,685 A * | 5/1989 | Haines | 604/30 |
| 5,242,404 A | 9/1993 | Conley et al. | 604/119 |
| 5,429,601 A * | 7/1995 | Conley et al. | 604/65 |
| 5,810,765 A * | 9/1998 | Oda | 604/31 |
| 5,897,524 A | 4/1999 | Wortrich | |
| 6,083,195 A | 7/2000 | Perkins et al. | 604/30 |
| 6,224,583 B1 | 5/2001 | Perkins et al. | 604/408 |
| 6,599,271 B1 | 7/2003 | Easley | 604/119 |
| 7,083,591 B2 | 8/2006 | Cionni | 604/31 |
| 2003/0108429 A1* | 6/2003 | Angelini et al. | 417/3 |
| 2006/0078448 A1 | 4/2006 | Holden | |
| 2006/0135974 A1 | 6/2006 | Perkins | 606/169 |
| 2007/0179438 A1 | 8/2007 | Morgan | 604/67 |

FOREIGN PATENT DOCUMENTS

| | | |
|---|---|---|
| DE | 37 13 420 A1 | 11/1988 |
| EP | 1 310 267 A | 5/2003 |
| WO | WO2006/119557 | 11/2006 |
| WO | WO 2007/001859 A | 1/2007 |
| WO | WO 2007/001929 A | 1/2007 |

OTHER PUBLICATIONS

International Search Report (PCTISA/210) and Written Opinion (PCT/ISA/237) mailed on May 11, 2009.

* cited by examiner

*Primary Examiner* — Kami A Bosworth
(74) *Attorney, Agent, or Firm* — Michael L. Smith

(57) ABSTRACT

The present invention provides a surgical system 10 for aspiration of a biological material comprising a source of irrigation fluid 20, a collection cassette 30, a pump 40 for creating a vacuum in the collection cassette 30, a handpiece 50 applied to a surgical area for infusing irrigation fluid and for aspirating a biological material, conduits 60 and 62 connecting the handpiece to each of the source of irrigation fluid and the collection cassette and means 70 for isolating the pump from the handpiece to prevent creation of vacuum within the conduit 62 and the collection cassette 30 after receiving a stop signal.

9 Claims, 2 Drawing Sheets

SURGICAL SYSTEM HAVING MEANS FOR ISOLATING VACUUM PUMP

FIELD

The present invention relates generally to a system useful for various surgical procedures. More specifically, it relates to a surgical system having means for assisting air venting or pressure regulation in an ophthalmic surgical procedure.

BACKGROUND

A cataract is an opacity that develops in the crystalline lens of the eye or in its envelope. One medical procedure to remove a cataract-affected lens is phacoemulsification (phaco) using ultrasonic sound to break up or emulsify the cataract. A phacoemulsification machine typically includes a handpiece with both irrigation and aspiration functions. A phaco handpiece aspirates in emulsified fluids and simultaneously replaces those aspired fluids with balanced salt solution (BSS) to maintain a proper pressure of the anterior chamber of the patient's eye. Such a handpiece is connected to a pump generating negative pressure or vacuum to drive aspiration, by which debris from the eye flow through a tube to means for collection such as a cassette, a bag, or a bottle.

A common and potentially dangerous occurrence in ophthalmic surgery is "post-occlusion surge." During ophthalmic surgery, particularly cataract surgery, as the lens is broken-up and emulsified, such as during phacoemulsification, irrigation fluid is constantly infused into the surgical site and the fluid and emulsified tissue are aspirated away from the surgical site through the phaco handpiece. On occasion bits of tissue are larger than the aspiration lumen in the phaco handpiece, which can result in a clogged phaco needle. As long as the aspiration conduit remains clogged, a negative pressure builds up throughout the aspiration system. Then, after the clog has been removed, the system can experience what is commonly referred to as surge. Post-occlusion surge can cause serious damage to a patient's eye, such as by rupturing a capsular bag and allowing vitreous to leak from the eye's posterior into the eye's anterior chamber or cause irreparable damage to the cornea's endothelial cells. Generally speaking, endothelial cells are not regenerated naturally and it is crucial to prevent post-occlusion surge in an ophthalmic operation.

Air evacuating pumps, such as a rotary vane pump and a venturi pump, are widely used as sources of vacuum for surgical aspiration. In the case of a rotary pump, for example, spinning of the rotor is necessary to force fluid to move through a tube to a reservoir where the spinning of the rotor generates vacuum to drive aspiration. One way to reduce post-occlusion surge is to sense an occlusion at the tip of the handpiece or the conduit and direct the pump to stop so that vacuum is not generated any more.

Another approach is to monitor and control the fluidic pressure automatically to reduce excessive negative pressure. For example, U.S. Pat. No. 3,902,495 describes a control system containing a relief valve discharging undue pressure from the tube upon reaching a predetermined pressure.

However, the methods mentioned above and other conventional pressure controlling methods failed to recognize or solve the problem that disconnection of an energy source, such as turning off the vacuum pump, or introducing a relief valve does not lead to an immediate stop because the pump has momentum to continue its motion. Such momentum continues to generate negative pressure notwithstanding the disconnection of the energy source of the pump, resulting in a delay in ceasing the generation at a negative pressure and the stop signal. Given that the anterior chamber is considerably small in volume, the delay in stopping the pump can cause damage to the eye. Therefore, there is a need to eliminate or reduce such an undesirable effect arising from momentum-driven pumping in ophthalmic surgery.

SUMMARY OF THE INVENTION

It is therefore one of the objects of this invention to provide a surgical system that does not generate momentum-driven vacuum after receiving a stop signal so as to prevent post-occlusion surge efficiently during eye surgery.

In one embodiment, it is provided a surgical system comprising means for isolating a vacuum pump from a handpiece to remove the undesirable effect of momentum-driven pumping after a stop signal.

In another embodiment, it is provided a surgical system for ophthalmic surgery comprising means for isolating a vacuum pump from a handpiece to remove the undesirable effect of momentum-driven pumping after a stop signal.

Yet in another embodiment, it is provided an ophthalmic surgical system for cataract surgery comprising means for isolating a vacuum pump from a phaco handpiece to remove the undesirable effect of momentum-driven pumping after a stop signal.

In another embodiment, it is provided a surgical system comprising means for isolating a vacuum pump from a handpiece and a controller to monitor the intra-conduit pressure of the system and send a stop signal to the means for isolating.

In yet another embodiment, it is provided a surgical system for ophthalmic surgery comprising means for isolating a vacuum pump from a phaco handpiece and a controller to monitor the intra-conduit pressure of the system and send a stop signal to the means for isolating.

In another embodiment, it is provided a surgical system comprising means for isolating a vacuum pump from a handpiece, one or more pressure relief valves to ease the pressure and a controller to monitor the intra-conduit pressure of the system and send a stop signal to the means for isolating and/or the relief valves.

In another embodiment, it is provided a system for ophthalmic surgery comprising means for isolating a vacuum pump from a phaco handpiece, one or more pressure relief valves to ease the pressure and a controller to monitor the intra-conduit pressure of the system and send a stop signal to the means for isolating and the relief valves.

DETAILED DESCRIPTION

The following description is merely exemplary in nature and is not intended to limit the present disclosure, application, or uses.

Figure 1:
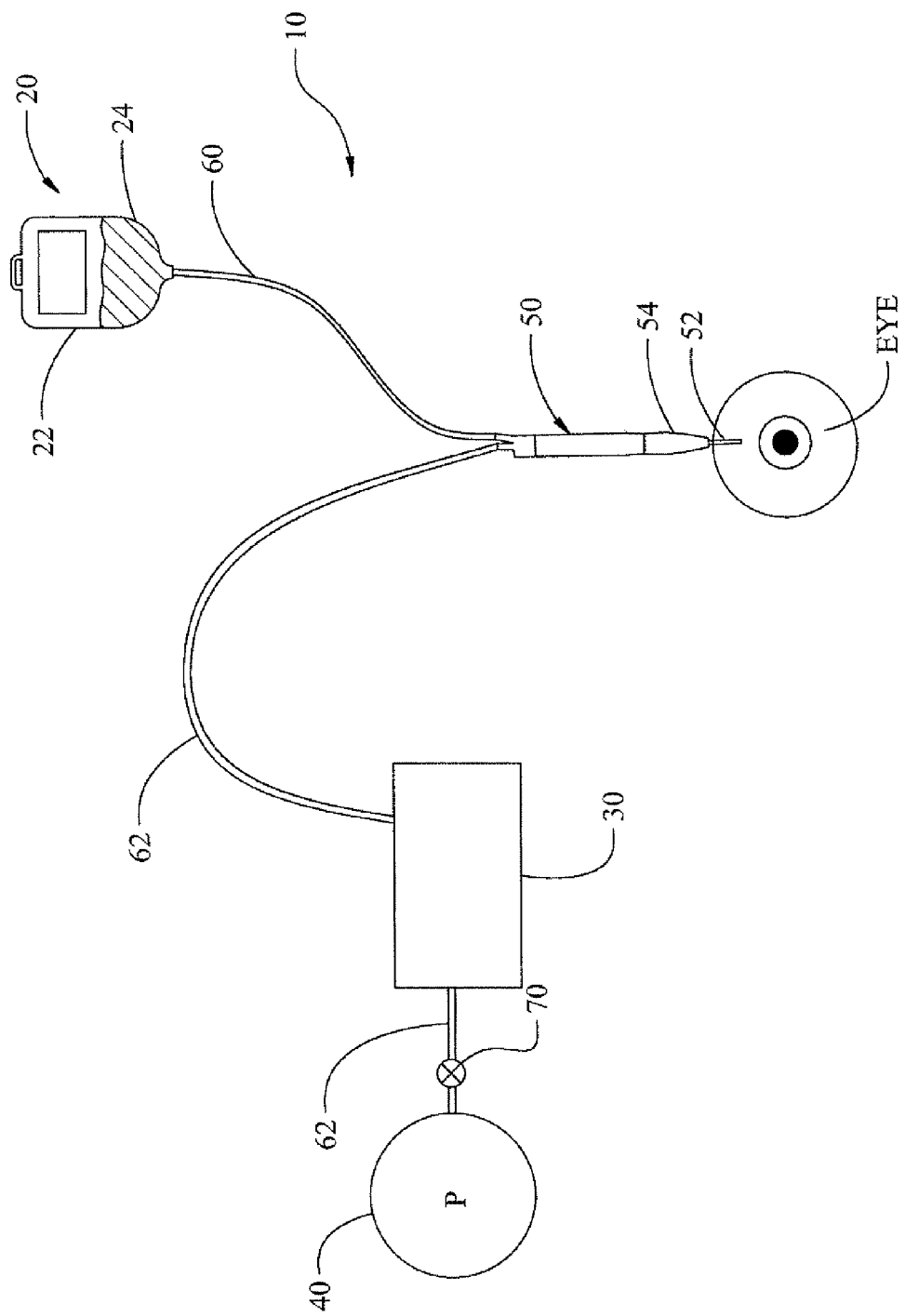
FIG. 1 is a diagrammatic view of one embodiment of a surgical system comprising means for isolating a vacuum pump.

Referring to FIG. 1, the surgical system 10 comprises a source of irrigation fluid 20, a collection cassette 30, a vacuum pump 40, a surgical handpiece 50, conduits 60 and 62 connecting the surgical handpiece to each of the irrigation fluid source and the vacuum pump/the collection cassette and means for isolating the pump 70 from the handpiece 50. The surgical system 10 is particularly useful in ophthalmic surgery where it is necessary to break up and remove undesirable biological materials from the patient's eye. Specifically, the surgical system 10 can be used to remove cataract without causing irreparable damage to the eye.

The source of irrigation fluid 20 typically includes a fluid container 22 and surgical fluid 24. The surgical fluid can be any known surgical fluid and an ordinary skilled person in the art can select proper surgical fluid in accordance with the nature of the surgery to be operated. In an ophthalmic surgical system, the surgical fluid 24 is ophthalmic surgical fluid such as, for example, BSS. Each end of the conduit 60 is connected to the container 22 and the phaco handpiece 50 respectively so that the ophthalmic surgical fluid is delivered to the patient's eye through the irrigation sleeve 54 of the phaco handpiece 50.

The collection cassette 30 typically has a collection chamber and an inlet and an outlet for connection to each of the handpiece 50 and the vacuum pump 40. The collection chamber accommodates biological debris aspirated from the surgical site via the phaco needle 52 of the handpiece 50 and the aspiration conduit 62. The collection cassette 30 can be selected from any collection means for a surgical system known in the art, regardless of its reusability. Thus, the cassette 30 can be any known reusable or disposable collection means. For safety and sanity of the operation, it may be preferable to select a collection cassette equipped with a fluid level detection device which is designed to prevent overflowing and leaking surgical fluids. The collection cassette 30 is installed in operative association with the handpiece 50 and the pump 40 by any means known in the art.

The vacuum pump 40 is connected to the collection cassette 30 and the handpiece 40 through the aspiration conduit 62 to provide the aspiration system comprising the handpiece, the conduit and the collection cassette with negative pressure or vacuum. The vacuum pump 40 can be any pump known in the art as long as it is suitable for a surgical system including the present surgical system. Preferably, the vacuum pump 40 is one suitable for an ophthalmic surgical system, Examples of a pump applicable to the present invention are, but not limited to, a venturi pump, a rotary vane pump, a diaphragm pump, a liquid ring pump, a piston pump, a scroll pump, a screw pump, Wankel pump, an external vane pump, a booster pump, a multistage roots pump, a peristaltic pump, and a Toepler pump. Preferably, the pump is selected from a venturi pump, a rotary vane pump and diaphragm pump.

The surgical handpiece 50 can be a conventional phacoemulsification handpiece comprising a phaco needle 52 and an annular sleeve for irrigation 54 surrounding the needle. The surgical handpiece is placed on or into the surgical site to remove undesirable biological materials. In an ophthalmic surgical system, for example, the phaco handpiece 50 is inserted though an incision in an eye and the phaco needle coupled to an energy source applies energy, such as ultrasound and laser, to the surgical site to break up undesirable biological materials such as cataract. The surgical fluid 24 is infused into the surgical site through the annular sleeve 54 and the phaco needle 52 simultaneously aspirates fluids containing the undesirable materials away from the eye.

The surgical system 10 typically requires two separate conduits 60 and 62 for the irrigation and aspiration system. The irrigation conduit 60 connects the surgical handpiece 50 to the irrigation fluid source 20 to provide the surgical site with the surgical fluid 24, such as BSS, The irrigation system may contain one or more valves placeable between the handpiece 50 and the irrigation fluid source 20 to control the irrigation flow rate, thereby helping maintenance of a proper pressure of the surgical site.

The aspiration conduit 62 connects, for example, the surgical handpiece 50 to the collection cassette 30 and then to the vacuum pump 40, but it is obvious to an ordinary skilled person in the art that it is possible to modify the placement and the connection of the aspiration components. The vacuum pump 40 is operatively connected to the collection cassette 30 through the aspiration conduit 62 such that undesirable biological materials from the surgical site are aspirated to the collection cassette 30 for temporary storage and later disposal.

The means for isolating the pump 70 is placed between the vacuum pump 40 and the handpiece 50 such that operation of the means separates the vacuum pump 40 from the handpiece 50 and/or the collection cassette 30. It is obvious to an ordinary skilled person in the art that the isolation means 70 can be placeable anywhere in the aspiration system. Therefore, for example, the isolation means 70 can be placed between the cassette 30 and the pump 40 or between the cassette 30 and the handpiece 50. Furthermore, one or more isolating means 70 can be installed in a surgical system: for example, one between the pump 40 and the cassette 30 and the other between the cassette 30 and the handpiece 50. The means for isolating the pump 70 is designed to shut down the aspiration conduit 62 or divert the generated negative pressure away from the handpiece 50 and/or the collection cassette 30 upon receiving a stop signal. Accordingly, the isolating means 70 prevents residual creation of vacuum completely within the aspiration conduit 62 and/or the collection cassette 30 after receiving a stop signal. Preferably, the means for isolating the pump 70 is a valve suitable for shutting down the aspiration conduit 62 or diverting the generated negative pressure away from the handpiece 50 and/or the collection cassette 30. Therefore, the means for stopping the pump 70 can be a conventional valve selected from the group consisting of a gate valve, a butterfly valve, a ball valve, a 3-way valve and a 4-way valve.

Figure 2:
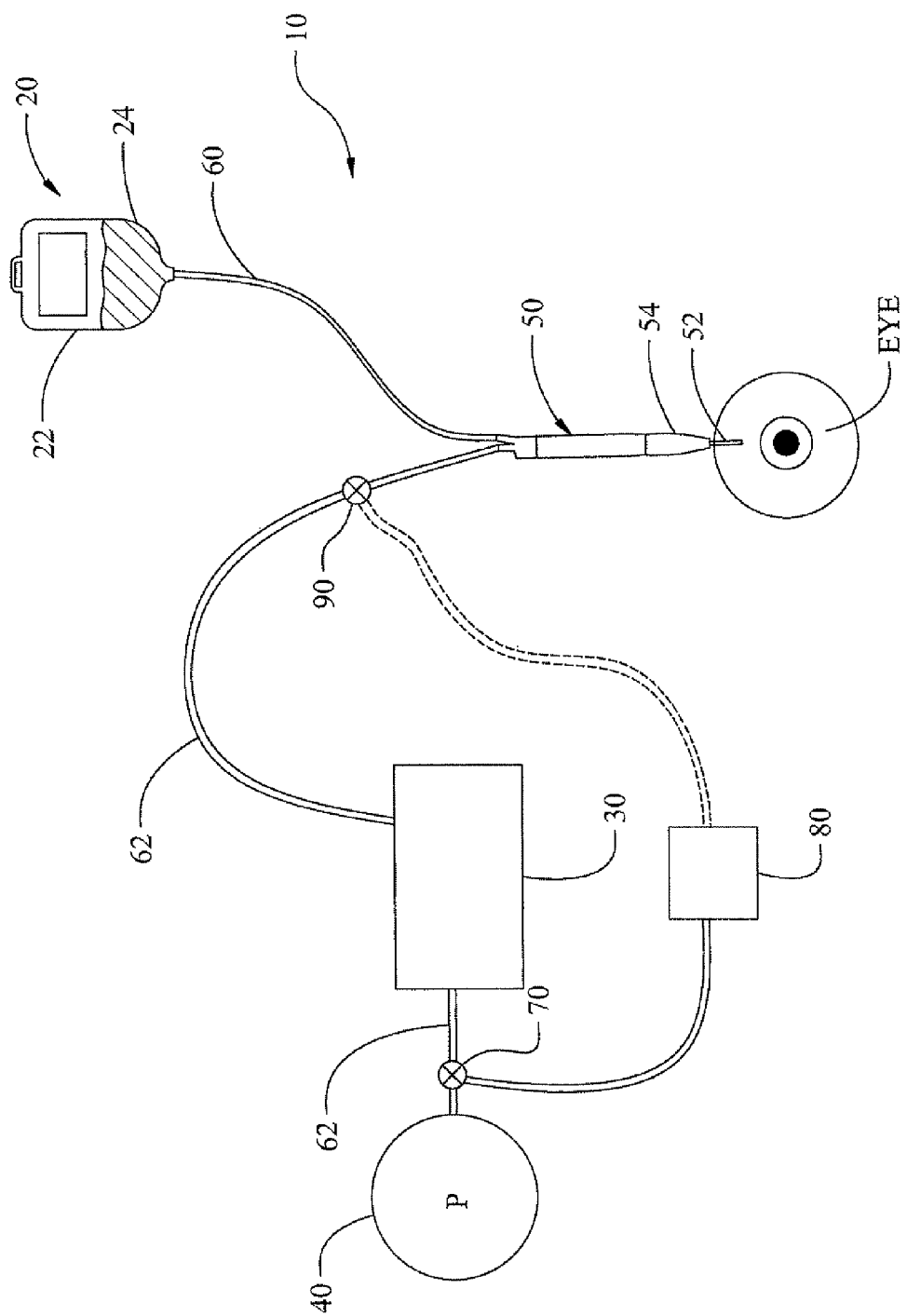
FIG. 2 is a diagrammatic view of another embodiment of a surgical system comprising means for isolating a vacuum pump, a controller and an optional pressure relief valve.

Referring to FIG. 2, the surgical system 10 comprises, in addition to the components illustrated in FIG. 1, a controller 80 which is connected to the means for isolating the pump 70. The controller 80 is designed to send a stop signal to the means for isolating the pump 70 when receiving a manual signal from an operator such as a surgeon or sensing a predetermined level of pressure difference that can lead to post-occlusion surge. For automation of the isolation process, the controller 80 may contain means for monitoring the pressure of the aspiration conduit 62 and means for sending a mechanical or electronic signal to the means for isolating the pump 70. Therefore, in one embodiment, the controller 80 contains a pressure transducer capable of measuring the vacuum level of the aspiration conduit 62 and generating a signal. The controller 80 can be computerized by electronic means to optimally control the surgical system based on various parameters where the electronic means determines the best timing for triggering the components to stop the aspiration system.

The surgical system 10 optionally comprises a pressure relief valve 90 connected to the aspiration conduit 62 to prevent post-occlusion surge in the surgical site such as the eye chamber. The pressure relief valve 90 can be a vacuum level control valve allowing an air flow into the aspiration conduit 62 at a pre-determined pressure. The surgical system 10 may have one or more pressure relief valves 90 to maximize the efficiency of preventing post-occlusion surge. In one embodiment, the controller 80 is linked to each of the means for isolating the pump 70 and the pressure relief valve 90 so that the controller 80 controls both components simultaneously. A stop signal generated by the controller 80 directs these components to work in unison to prevent post-occlusion surge. In such a system, one signal results in not only complete isolation of the vacuum pump 40, i.e., no creation of momentum-driven vacuum, but also reduction of the increased negative pressure within the aspiration conduit 62.

The embodiments are described in order to best explain the principles of the invention and its practical application to thereby enable others skilled in the art to best utilize the invention in various embodiments and with various modifications.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims and their equivalents.

What is claimed is:

1. A surgical system for aspiration of a biological material comprising
    a source of irrigation fluid;
    a collection cassette;
    a pump for creating a vacuum in the collection cassette;
    a handpiece for applying to a surgical area for infusing irrigation fluid and for aspirating a biological material;
    a conduit connecting the handpiece to each of the source of irrigation fluid and the collection cassette; and
    means connected between the pump and the collection cassette for isolating the pump from the handpiece to prevent creation of vacuum within the conduit and the collection cassette after receiving a stop signal.

2. The surgical system according to claim 1, wherein the means for isolating the pump is a mechanical means to shut down the conduit or divert the generated negative pressure away from the handpiece.

3. The surgical system according to claim 1, wherein the means for isolating the pump is a valve to shut down the conduit or divert the generated negative pressure away from the handpiece.

4. The surgical system according to claim 3, wherein the valve is selected from the group consisting of a ball valve, a gate valve, a butterfly valve, a 3-way valve and a 4-way valve.

5. The surgical system according to claim 1, further comprising a controller connected to the means for isolating the pump to send a stop signal to the means for isolating.

6. The surgical system according to claim 5, wherein the controller is a surge-flow regulator that monitors the pressure of the conduit and sends a stop signal to both the pump and the means for isolating upon reaching a pre-determined pressure.

7. The surgical system according to claim 1, further comprising one or more pressure relief valves.

8. The surgical system according to claim 7, further comprising a controller connected to each of the means for isolating the pump and the pressure relief valves, wherein the controller sends a mechanical or electronic stop signal to the pump and the means for isolating the pump and makes the pressure relief valves open upon sensing a pre-determined pressure.

9. The surgical system according to claim 1, wherein the surgical system is for ophthalmic surgery and the handpiece is a phacoemulsification handpiece for applying to a patient's eye.

\* \* \* \* \*